US011425861B2

(12) United States Patent
Bahadorani et al.

(10) Patent No.: US 11,425,861 B2
(45) Date of Patent: Aug. 30, 2022

(54) PROCESS AND UNIT FOR HARVESTING AND PROCESSING WATER HYACINTHS

(71) Applicant: IN-BETWEEN SA, Braine l'Alleud (BE)

(72) Inventors: Rebeka Bahadorani, Braine l'Alleud (BE); Pierre Bono, Sainte Savine (FR)

(73) Assignee: IN-BETWEEN SA, Braine l'Alleud (BE)

( * ) Notice: Subject to any disclaimer, the term of this patent is extended or adjusted under 35 U.S.C. 154(b) by 907 days.

(21) Appl. No.: 16/315,811

(22) PCT Filed: Jun. 8, 2017

(86) PCT No.: PCT/EP2017/063923
§ 371 (c)(1),
(2) Date: Jan. 7, 2019

(87) PCT Pub. No.: WO2018/007090
PCT Pub. Date: Jan. 11, 2018

(65) Prior Publication Data
US 2019/0208704 A1     Jul. 11, 2019

(30) Foreign Application Priority Data
Jul. 7, 2016 (FR) ...................................... 1656535

(51) Int. Cl.
| A01D 44/00 | (2006.01) |
| F26B 17/04 | (2006.01) |
| A61L 2/00 | (2006.01) |
| A61L 2/10 | (2006.01) |
| A61L 2/26 | (2006.01) |
| B02C 21/02 | (2006.01) |

(Continued)

(52) U.S. Cl.
CPC ............ *A01D 44/00* (2013.01); *A61L 2/0023* (2013.01); *A61L 2/10* (2013.01); *A61L 2/26* (2013.01);

(Continued)

(58) Field of Classification Search
CPC . A61L 2/10; A61L 2/26; A61L 2/0023; A61L 2202/17; A01D 44/00; B02C 21/026
See application file for complete search history.

(56) References Cited

U.S. PATENT DOCUMENTS

| 4,222,217 A | 9/1980 | Brown |
| 5,487,258 A | 1/1996 | McNabb |

(Continued)

FOREIGN PATENT DOCUMENTS

| CA | 2901500 A1 | 12/2014 |
| CN | 1268305 A | 10/2000 |

(Continued)

OTHER PUBLICATIONS

Chinese Office Action and Search Report dated Jun. 24, 2021 in counterpart application No. CN201780039369.5; w/English machine translation (total 17 pages).

(Continued)

*Primary Examiner* — Sean E Conley
(74) *Attorney, Agent, or Firm* — Seckel IP, PLLC

(57) ABSTRACT

Method for harvesting and processing water hyacinths, characterized in that the following steps are performed: a) the water hyacinths growing in an aquatic medium are cut; b) the water hyacinths are collected on board a barge at berth (1); c) the collected water hyacinths are transferred onto draining racks (2) near the quayside; d) the drained hyacinths are washed with clean water; e) the washed water hyacinths are drained on vibrating belts (7) in order to remove some of the excess water; f) the water hyacinths are dried on a dryer (8) at a temperature of between 50 and 100° C. for 5 to 17 h; g) the water hyacinths and their seeds are steam-sterilised at a temperature of between 80 and 100° C. in order to sterilise them; h) the sterilised water hyacinths and seeds are ground in order to make profitable use thereof.

20 Claims, 2 Drawing Sheets

Figure 1:
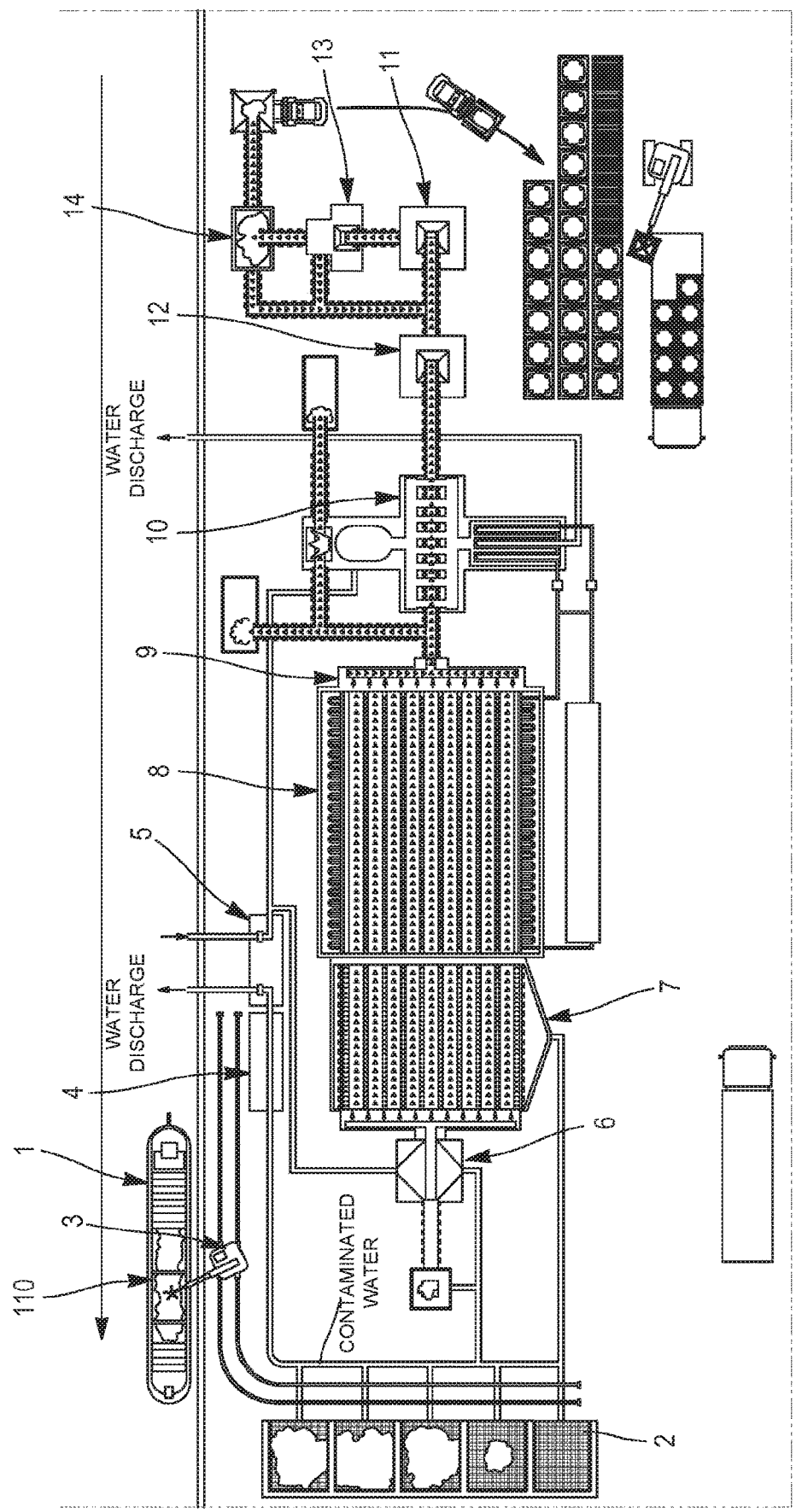

(51) Int. Cl.
  *C02F 1/00* (2006.01)
  *C02F 1/32* (2006.01)
  *F26B 17/08* (2006.01)
  *B02C 23/18* (2006.01)
  *B08B 3/14* (2006.01)
  *F26B 15/14* (2006.01)
  *C02F 103/26* (2006.01)

(52) U.S. Cl.
  CPC ............ *B02C 21/026* (2013.01); *B02C 23/18* (2013.01); *B08B 3/14* (2013.01); *C02F 1/001* (2013.01); *C02F 1/32* (2013.01); *F26B 15/146* (2013.01); *F26B 17/045* (2013.01); *A61L 2202/17* (2013.01); *C02F 2103/26* (2013.01); *C02F 2303/04* (2013.01); *F26B 17/08* (2013.01)

(56) References Cited

U.S. PATENT DOCUMENTS

| | | |
|---|---|---|
| 2006/0150493 A1 | 7/2006 | Van Deventer |
| 2017/0268192 A1 | 9/2017 | Biley et al. |

FOREIGN PATENT DOCUMENTS

| | | |
|---|---|---|
| CN | 2749243 Y | 1/2006 |
| CN | 102689337 A | 9/2012 |
| CN | 202857322 U | 4/2013 |
| CN | 103444398 A | 12/2013 |
| CN | 104012523 A | 9/2014 |
| CN | 105493742 A | 4/2016 |
| GB | 369263 A | 3/1932 |
| WO | 92/21227 A2 | 12/1992 |

OTHER PUBLICATIONS

International Search Report and Written Opinion dated Aug. 4, 2017 issued in corresponding application No. PCT/EP2017/063923; w/ English partial translation and partial machine translation (19 pages).

Indian Office Action dated Apr. 24, 2021 in counterpart application No. IN201917004881; in English (total 7 pages) (note: D2-D5 cited in the Indian Office Action are not listed in this IDS since they were already listed in the IDS filed Jan. 7, 2019).

PROCESS AND UNIT FOR HARVESTING AND PROCESSING WATER HYACINTHS

The present invention falls within the field of the methods for harvesting and processing water hyacinths.

The water hyacinth or "*Eichhornia crassipes*" is a freshwater aquatic plant, of the aquatic macrophyte type. This plant species is very invasive. It raises a problem because of its rapid growth and during its decomposition. Indeed, its rapid and widespread growth has an impact on the freshwater ecosystem. The spread of the water hyacinth in its environment can namely smother the native species by forming, at the level of the lower strata, monospecific dense carpets, depriving them of vital light.

In addition, during its decomposition, the water hyacinth releases, in its aquatic medium, nutrients that can lead to eutrophication or anoxia of the environment, which represents a danger for aquatic biodiversity that can lead to the death of many species cohabiting with the water hyacinths.

In addition, the water hyacinth seeds are long-lasting, the time of dormancy of the seeds is twenty years. These seeds tolerate dryness and germinate as soon as they are immersed in the aquatic medium. Thus, even in case of harvest, during storage, there is a risk of contamination, i.e., seed germination, in particular when the storage environment is wet. Thus, it is necessary to be able to avoid this risk of germination of water hyacinth seeds during storage in order to allow their profitable use in the industrial environment.

Therefore, in order to avoid the aforementioned phenomena, it is necessary to find an easy and quick solution for harvesting, processing and profitably using the water hyacinth in the industry.

The present invention aims to cope with the drawbacks of the state of the art, by providing a method for harvesting and processing water hyacinths, in which the following steps are performed:

a) the water hyacinths growing in an aquatic medium are cut;
b) the water hyacinths are collected aboard a barge at berth;
c) the collected water hyacinths are transferred onto draining means, such as draining racks, near the quayside;
d) the drained hyacinths are washed with clean water;
e) the washed hyacinths are drained on vibrating belts in order to partially eliminate the excess water;
f) the water hyacinths are dried on a dryer at a temperature between 50 and 100° C. for a period between 5 h and 17 h;
g) steam sterilization at 80 to 100° C. is performed, in order to sterilize the water hyacinths and their seeds;
h) the sterilized water hyacinths and their seeds are ground in order to make them profitable for use.

In addition, according to further features of the method of the invention:

the residual water resulting from the draining of step c) is recovered, said residual water is processed by UV sterilization in a purification plant in order to be discharged into the original aquatic medium of the water hyacinths;
the clean water of step d) consists of water withdrawn from the original aquatic medium of the water hyacinths, said withdrawn water being pumped by means of a pumping plant and filtered through a filtering grid comprising an opening diameter between 6 and 10 mm so as to make it clean for the washing step;
step d) is performed by washing at least twice with clean water the drained hyacinths in washing means, such as a washing container;
after the sterilization step g) and prior to the grinding step h), the sterilized water hyacinths are dried by a forced hot-air system;
after the grinding step (h), a micronization of the obtained ground materials is performed in order to allow their profitable use in the field of plastics processing or insulation materials;
the drying step f) is performed using a vertical hot-air dryer;
after the drying step f) and prior to the sterilization step g), the dried water hyacinths are concentrated in concentration means, such as a concentrator;
after step d) of washing said drained water hyacinths, the latter are cut into at least three or four lengths.

The present invention also relates to a unit for harvesting and processing water hyacinths permitting to perform the method of the invention and in this order:

a floating barge near the quayside, said barge being equipped with means for cutting the water hyacinths, means for collecting and storing the cut water hyacinths, and means for transferring said water hyacinths to the quayside, said transfer means being aimed at transferring said water hyacinths onto draining means for draining the collected water hyacinths;
means for moving the drained water hyacinths to washing means connected to additional draining means;
drying means at the exit of said additional draining means;
means for concentrating the dried water hyacinths at the exit of said drying means;
means for sterilizing the concentrated water hyacinths at the exit of said concentration means;
means for grinding the sterilized water hyacinths at the exit of said sterilization means.

Figure 2:
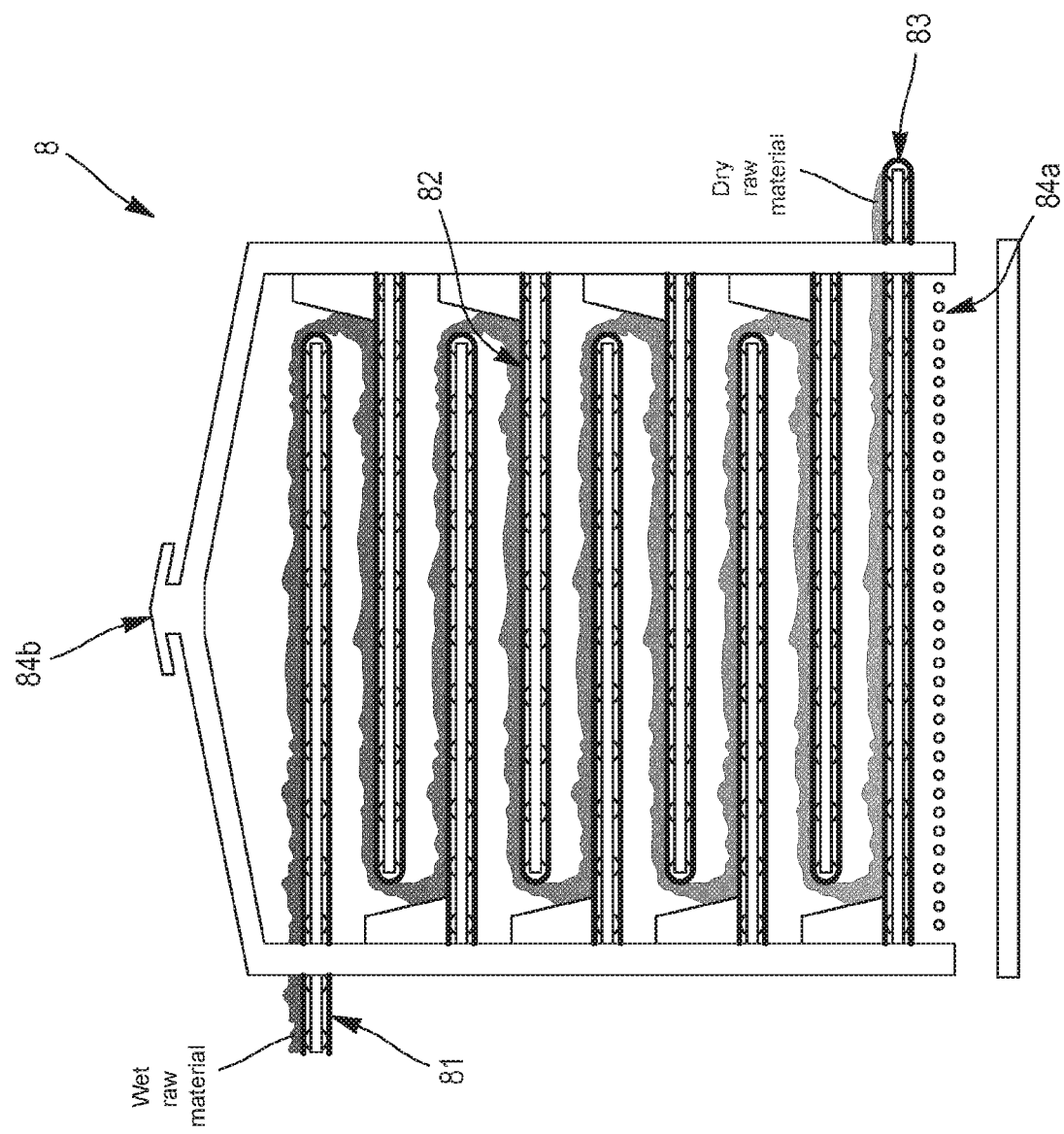

Further features and advantages of the invention will become clear from the following detailed description of non-restrictive embodiments of the invention, when referring to the attached figures, in which:

FIG. 1 schematically shows a view of the unit for harvesting and processing water hyacinths;
FIG. 2 schematically shows a view of the vertical hot-air dryer of the unit for harvesting and processing water hyacinths.

The present invention relates to a method for harvesting and processing water hyacinths.

The harvesting of water hyacinths occurs by means of a floating barge 1 equipped with means for cutting, means for collecting and storing 110 cut water hyacinths.

Thus, the implementation of the method of the invention occurs by successively performing the following steps:

a) the water hyacinths growing in an aquatic medium are cut;
b) the water hyacinths are collected aboard a barge 1 at berth.

Once they have been harvested, the method of the invention permits to transfer the collected water hyacinths onto draining means 2, namely draining racks 2, near the quayside.

The transfer of the harvested water hyacinths is performed using transfer means 3. According to a particular embodiment, when the ground allows the installation of rails, the transfer means 3 may consist in particular of rotating telescopic carriages capable of transferring the hyacinths from the boat to the draining racks 2 on the quayside.

Advantageously, the draining racks 2 are positioned near the quayside bordering the aquatic medium.

According to a particular embodiment, the draining racks 2 consist of stainless metal grids which are raised relative to the ground.

The stainless nature is essential to prevent premature wear of the draining racks 2 by the excess water and to avoid corrosion and degradation due to rust.

Draining the harvested water hyacinths permits a first coarse removal of excess water in order to facilitate the processing of the hyacinths.

According to a particular embodiment of the invention, the excess water, i.e., the residual water from the draining, is recovered. Then, said residual water is processed by UV sterilization in a purification plant 4, for its discharge afterwards into the original aquatic medium of the water hyacinths.

After this first coarse draining on the draining racks 2, the drained water hyacinths are washed with clean water. According to a particular embodiment, the clean washing water consists of water withdrawn from the original aquatic medium of the water hyacinths. Said withdrawn water is pumped by means of a pumping plant 5 and filtered on fine gratings with a separation diameter between 6 and 10 mm. Then, said water is sieved on fine gratings with perforations between 4 and 6 mm in order to make it clean for the washing step.

Advantageously, the washing is performed using washing means 6, in particular in a washing container 6, with clean water.

Advantageously, the washing operation is repeated several times.

Advantageously, the same quantity of material is washed at least twice. Nevertheless, depending on the pollution and the composition of the aquatic medium where the hyacinths were withdrawn, i.e., depending on the dirt of said aquatic living medium of the water hyacinths, additional washing cycles will be necessary. These washing cycles can reach up to ten successive washing cycles.

The washing step permits to remove the impurities bound to and still present in the slack of drained water hyacinths and to purify them coarsely.

After washing, the washed water hyacinths are dried on a vibrating belt 7 in order to partially remove the excess wash water and to obtain the least hydrated possible material.

According to a particular embodiment of the invention, the vibrating belts 7 are in the form of vibrating draining racks inclined at about 5° and the filtering grid of which has openings with a decreasing diameter ranging from 2 to 0.2 mm.

Advantageously, the material, i.e., the washed water hyacinth, is drained on a series of vibrating conveyor belts 7 of stainless metal mesh, as shown in FIG. 1.

According to a particular embodiment, the water residues, after passing on the vibrating conveyor belts 7, are recovered for being UV sterilized and released into the aquatic medium.

According to the invention, the water hyacinths are dried using drying means 8, in particular on a dryer 8. Drying occurs at a temperature between 50 and 110° C. for a period between 5 h and 16 h.

According to a specific embodiment, said drying of the water hyacinths is performed at a temperature between 50 and 70° C. for a period between 14 h and 16 h.

According to another preferred embodiment, said drying of the water hyacinths is performed at a temperature between 90 and 110° C. for a period between 5 h and 7 h.

In all cases, the drying must be performed at a temperature lower than 110° C., in order to avoid damaging the fibers of the hyacinths.

According to a particular embodiment, said dryer 8 consists of a solar-powered vertical hot-air dryer 8, in particular for saving energy necessary for its operation, or powered by any other power supply system.

According to this particular embodiment and as illustrated in FIG. 2, this vertical hot-air dryer 8 includes:

- in the upper portion an inlet 81, such as a conduit, permitting the incorporation of the wet washed material to be dried;
- over its full height, a series of meshed stainless steel conveyor belts 82 that vibrate and permit the gradual transport, from top to bottom, of the material to be dried, the grids permitting the passage of air;
- in the lower portion, an outlet 83, such as a conduit, permitting the evacuation of the dried material, i.e., the dried water hyacinths, to the outside of the vertical hot-air dryer 8.

It should be noted that the conveyor belts 82 are vibrating and thus avoid a static drying of the material. Indeed, a static drying is slower and less efficient than a dynamic drying by vibration.

In said vertical hot-air dryer 8, the presence in the lower portion of an air-inlet system 84a and in the upper portion of an air-outlet opening 84b will permit to gradually dry the material. The air circulation inside the dryer will thus facilitate the drying. In this dryer 8, the hot-air circulation, which is possible over the entire height, namely through the grids, will permit a gradual drying of the material. The hot air circulating through the dryer 8 has a temperature between 50 and 110° C.

At the exit 83 of the dryer 8, the dried material is recovered and the dried water hyacinths are concentrated using concentration means 9, in particular in a concentrator 9. The use of the concentrator 9 permits to improve the line of action and flow of the matter.

After passing through the dryer 8, the concentrated material is sterilized with steam at a temperature between 80 and 100° C., in order to sterilize the dried water hyacinths and their seeds. The sterilization is performed using steam sterilization means 10, in particular in a steam sterilizer 10.

This sterilization method and the temperature range used permit to avoid a germination of the water hyacinth seeds and their proliferation. The sterilization permits to prevent said possible germination, namely when the grinding step is performed.

According to the method of the invention, in order to finalize the processing of the dried water hyacinths, the sterilized water hyacinths and their seeds are ground, in order to be able to be profitably used later and at industrial level.

The grinding step is performed using grinding means 11, namely such as a grinder 11, permitting to obtain ground material having a grain size between 1 and 3 cm. This size of the ground material is necessary for ease of use in the industry, namely in the field of plastics processing and the insulation materials.

According to a particular embodiment, in order to optimize the grinding and to obtain the driest possible material, with a dry matter hydration rate of less than 20% RH or "Relative Humidity", it is possible to perform, after the sterilization step g) and prior to the grinding step h), a drying by ventilation of the sterilized material, i.e., the sterilized water hyacinth, by a forced hot-air system. This drying by ventilation is performed in a forced air dryer 12.

The forced hot-air system permits to further dehydrate the sterilized hyacinth, namely by bringing it into contact with hot air at a temperature between 50 and 70° C.

According to another specific embodiment of the invention, after the grinding step h) is performed a micronization of the obtained ground materials, in order to permit their profitable use in the field of plastics processing and the insulation materials.

The micronization is performed in a micronizer 13 permitting to obtain a grain size of the ground materials of less than 1 mm.

This type of ground materials with very small grain size is easy to be profitable used.

According to another embodiment of the invention, the ground water hyacinth materials can be sieved using a sieve 14 for their grain shape to be easy to be used. The refusal of the sieve 14 can be used as fuel for supplying a steam boiler, thus permitting the operation of the steam sterilizer 10.

The present invention also relates to a unit for harvesting and processing the water hyacinths illustrated in FIG. 1, comprising in this order:
- a floating barge (1) near the quayside, said barge (1) being equipped with means for cutting the water hyacinths, means for collecting and storing (110) the cut water hyacinths, and means for transferring (3) said water hyacinths to the quayside, said transfer means (3) being aimed at transferring said water hyacinths onto the draining means (2) aimed at draining the collected water hyacinths;
  - means for moving the drained water hyacinths to washing means (6) connected to additional draining means;
  - drying means (8) at the exit of said additional draining means;
  - means (9) for concentrating the dried water hyacinths at the exit of said drying means (8);
  - means for sterilizing (10) the concentrated water hyacinths at the exit of said concentrating means (9),
  - means for grinding (11) the sterilized water hyacinths at the exit of said sterilization means (10).

According to a particular embodiment, the unit for harvesting and processing the water hyacinths may in addition include, at the exit of the steam sterilizer 10, a dryer 12 for further eliminating the remaining water.

According to another particular embodiment of the invention, at the exit of the grinder 11, the ground materials of the dehydrated water hyacinths are micronized in a micronizer 13, then, optionally, the micronized ground materials are sieved using a sieve 14. Thus, this specific processing permits to facilitate their profitable industrial use, the obtained micronized and/or sieved hyacinth "powder" being stable, inert, without risk of germination and easily transportable.

Thus, the unit for harvesting and processing the water hyacinths permits both to harvest and process the water hyacinths by transforming them into ground materials profitably used in the industry. Said obtained ground materials have such a low hydration rate, almost zero, that the risk of germination during storage has been eliminated. Thus, the ground materials are durable and inert, they can be used in the industry, for example in the field of plastics processing or the manufacture of insulation panels.

The method for harvesting and processing the water hyacinths and its harvesting unit represent a solution easy to be implemented for eliminating the pollution of the aquatic mediums and for eliminating the water hyacinths. The method and the harvesting unit of the invention also permit a rapid and efficient processing of the harvested water hyacinths in order to be able to be profitably used at industrial level.

The invention claimed is:

1. A method for harvesting and processing water hyacinths, comprising:
   a) cutting the water hyacinths growing in an aquatic medium;
   b) collecting the water hyacinths aboard a barge at berth on a quayside;
   transferring the collected water hyacinths near the quayside and draining of the water hyacinths;
   d) washing the drained hyacinths with clean water;
   e) performing an additional draining the washed hyacinths on vibrating belts in order to at least partially eliminate excess water;
   f) drying the water hyacinths on a dryer at a temperature in a range of from 50 to 100° C. for a period in a range of from 5 hours to 17 hours;
   g) performing steam sterilization at a temperature in a range of from 80 to 100° C. in order to sterilize the water hyacinths and their seeds;
   h) grinding the sterilized water hyacinths and their seeds in order to make them adapted for further use.

2. The method for harvesting and processing water hyacinths according to claim 1, comprising recovering residual water from the first draining, and processing the residual water by UV sterilization within a purification plant in order to discharge the residual water into the original aquatic medium of the water hyacinths.

3. The method for harvesting and processing water hyacinths according to claim 1, wherein the clean water of the washing includes water withdrawn from the original aquatic medium of the water hyacinths, the withdrawn water being pumped by a pumping plant and filtered through a filtering grid comprising an opening diameter in a range of from 6 to 10 mm so as to make the filtered water clean for the washing.

4. The method for harvesting and processing water hyacinths according to claim 1, wherein the washing is performed by washing the drained hyacinths at least twice with the clean water.

5. The method for harvesting and processing water hyacinths according to claim 1, comprising, after the sterilizing and prior to the grinding, performing an additional drying of the sterilized water hyacinths.

6. The method for harvesting and processing water hyacinths according to claim 1, comprising, after the grinding, performing a micronization of the a ground material obtained from the grinding in order to permit further use of the ground material in the field of plastics processing or insulation materials.

7. The method for harvesting and processing water hyacinths according to claim 1, wherein the drying is performed using a hot-air dryer.

8. The method for harvesting and processing hyacinths according to claim 1, comprising, after the drying and prior to the sterilizing, concentrating the dried water hyacinths.

9. The method for harvesting and processing water hyacinths according to claim 1, comprising, after the washing, performing an additional cutting of the water hyacinths into at least three lengths.

10. A unit for harvesting and processing water hyacinths, wherein the unit comprises:
    a floating barge near a quayside, the barge being adapted for collection and storage of cut water hyacinths, and for transferring the water hyacinths to the quayside;

draining means adapted for receiving the water hyacinths transferred from the floating barge and for draining the collected water hyacinths;

washing means adapted for receiving the water hyacinths moved from the draining means;

additional draining means adapted for receiving the water hyacinths moved from the washing means;

drying means at an exit of the additional draining means;

means for concentrating the dried water hyacinths at an exit of the drying means;

means for sterilizing the concentrated water hyacinth at an exit of the concentrating means;

means for grinding the sterilized water hyacinths at an exit of the sterilization means.

11. The method for harvesting and processing water hyacinths according to claim 1, wherein, in the transferring, the collected water hyacinths are transferred onto draining means.

12. The method for harvesting and processing water hyacinths according to claim 11, wherein the draining means is a draining rack.

13. The method for harvesting and processing water hyacinths according to claim 1, wherein the washing is performed by washing the drained hyacinths with the clean water in washing means.

14. The method for harvesting and processing water hyacinths according to claim 13, wherein the washing means is a washing container.

15. The method for harvesting and processing water hyacinths according to claim 4, wherein the washing is performed by washing the drained hyacinths with the clean water in washing means.

16. The method for harvesting and processing water hyacinths according to claim 15, wherein the washing means is a washing container.

17. The method for harvesting and processing water hyacinths according to claim 5, wherein the additional drying of the sterilized water hyacinths is performed by a forced hot-air system.

18. The method for harvesting and processing water hyacinths according to claim 7, wherein the hot-air dryer is a vertical hot-air dryer.

19. The method for harvesting and processing hyacinths according to claim 1, wherein the concentrating of the dried water hyacinths is performed in concentrating means.

20. The method for harvesting and processing water hyacinths according to claim 19, wherein the concentrating means is a concentrator.

* * * * *